United States Patent [19]

Hatfield et al.

[11] Patent Number: 5,413,775
[45] Date of Patent: May 9, 1995

[54] HAIRSPRAYS AND ACRYLIC POLYMER COMPOSITIONS FOR USE THEREIN

[75] Inventors: James C. Hatfield, St. Albans, W. Va.; Steven I. Cochran, Franklin Park, N.J.; David R. Bassett, Charleston, W. Va.; Raymond Rigoletto, Jr., Wanamassa, N.J.

[73] Assignee: Amerchol Corporation, Edison, N.J.

[21] Appl. No.: 953,496

[22] Filed: Sep. 29, 1992

[51] Int. Cl.⁶ .................. A61K 7/11; A61K 7/075; A61K 9/16; C08F 218/10
[52] U.S. Cl. .................... 424/47; 424/70.16; 424/70.11; 424/DIG. 1; 424/DIG. 2; 424/500; 526/318.4; 526/909; 526/936
[58] Field of Search ........... 424/47, 70, 71, DIG. 1, 424/DIG. 2, 500; 526/318.4, 909, 911, 932, 936

[56] References Cited

U.S. PATENT DOCUMENTS

| | | | |
|---|---|---|---|
| 3,577,517 | 5/1971 | Kubot et al. | 424/27 |
| 3,660,561 | 5/1972 | Shepherd et al. | 424/27 |
| 3,726,288 | 4/1973 | Novak et al. | 132/7 |
| 3,740,367 | 6/1973 | Winkelblech | 260/29.6 |
| 3,980,602 | 9/1976 | Jakubauskas | 524/561 |
| 4,085,264 | 4/1978 | Seib et al. | 525/360 |
| 4,139,514 | 2/1979 | Bassett | 524/831 |
| 4,192,861 | 3/1980 | Micchelli et al. | 424/47 |
| 4,196,190 | 4/1980 | Gehman et al. | 424/47 |
| 4,288,427 | 9/1981 | Farmer, III et al. | 424/70 |
| 4,316,929 | 2/1982 | McIntire et al. | 524/300 |
| 4,543,249 | 9/1985 | Nelson | 424/70 |
| 4,673,571 | 6/1987 | Mahieu et al. | 424/72 |
| 4,798,721 | 1/1989 | Yahagi et al. | 424/70 |
| 4,874,604 | 10/1989 | Sramek | 424/47 |
| 5,019,377 | 5/1991 | Torgerson | 424/70 |

FOREIGN PATENT DOCUMENTS

| | | | |
|---|---|---|---|
| 1110240 | 4/1968 | United Kingdom | A61K 7/00 |
| 1293529 | 10/1972 | United Kingdom | |

*Primary Examiner*—Edward J. Webman
*Attorney, Agent, or Firm*—Warren K. Volles

[57] ABSTRACT

Aqueous, anionic, acrylic polymer compositions comprising a copolymer of an alkyl acrylate, an alkyl methacrylate and one or more acrylate acids or salts thereof is disclosed. By controlling the particle size of the copolymer and introducing a surfactant, enhanced freeze-thaw stability can be obtained with the polymer compositions of the present invention. The polymer compositions are compatible in all-aqueous hairspray compositions, as well as those which contain up to about 80 weight percent volatile organic compounds, or more.

29 Claims, No Drawings

HAIRSPRAYS AND ACRYLIC POLYMER COMPOSITIONS FOR USE THEREIN

FIELD OF THE INVENTION

The present invention relates to aqueous, anionic, acrylic polymer compositions containing a copolymer of an alkyl acrylate, an alkyl methacrylate and one or more acrylate acids or salts thereof. The present invention also relates to hairspray compositions comprising such acrylic polymer compositions.

BACKGROUND OF THE INVENTION

Hairspray compositions typically contain copolymers as the active ingredient in addition to a carrier. The polymers are typically prepared from a variety of monomers, such as, for example, vinyls, acrylics, acrylamides, unsaturated dicarboxylics and anhydrides. Depending upon the particular monomers employed, the resulting polymers can be anionic, cationic or amphoteric. Typical carriers include lower alcohols, i.e., in the $C_2$ to $C_4$ carbon range, water and propellants such as alkanes in the $C_1$ to $C_4$ carbon range, ethers such as dimethyl ether and gases such as nitrogen and carbon dioxide.

It is not uncommon for the concentration of volatile organic compounds ("VOCs"), e.g., hydrocarbon carriers, to comprise a significant amount of the hairspray composition. Usually, the VOC content is about 80 weight percent or more. Many hairsprays are formulated with a VOC content of up to about 95 weight percent. As environmental regulations impose reductions on the amount of VOCs emitted to the atmosphere, hairspray compositions comprising lower levels of VOCs will be required.

Accordingly, in order to comply with changing environmental regulations, polymer compositions suitable for use in hairspray compositions are desired which will allow formulators to provide hairspray compositions comprising a wide range of VOC content. Moreover, it is desired that such hairspray compositions be deliverable from either pump systems or aerosol systems.

Furthermore, when hairspray compositions are formulated with low levels of VOCs, it is desired that such hairsprays, as well as the polymer compositions used therein, have acceptable freeze-thaw stability, i.e., ability to withstand cycles of freezing and thawing. Freeze-thaw stability is an important attribute of such polymer compositions and hairspray compositions because freezing can occur during transportation or storage thereof.

Often, when aqueous based polymer compositions are subjected to freezing and thawing, a substantial increase in viscosity can occur. Such increases in viscosity can adversely affect the performance of the hairspray, e.g., pumpability, wetting, etc. Freeze-thaw stability can be obtained by introducing antifreeze ingredients, such as, for example, glycols and protective colloids such as hydroxyethyl cellulose and poly(vinylpyrrolidone), or by maintaining the pH at a moderate basicity, e.g., 8.5 or higher. However, introducing such other ingredients into the compositions, or increasing the pH to above about 8.5, may adversely affect other properties, e.g., drying time, curl retention and tackiness, and is therefore undesirable.

SUMMARY OF THE INVENTION

By the present invention, aqueous, anionic, polymer compositions are provided which are compatible with a wide range of carriers, e.g., those having a VOC content of 0 to 80 weight percent, or more. In addition, by virtue of the present invention, it is now possible to provide polymer compositions having excellent freeze-thaw stability by carefully controlling the particle size of the copolymer and introducing a surfactant effective to enhance freeze-thaw stability of the composition. When used in hairspray compositions, the polymer compositions of the present invention can provide excellent performance characteristics, e.g., curl retention, drying time, feel, shine, combability, tackiness and flaking resistance. The hairspray compositions of the present invention can be conveniently formulated to be delivered either by pump or aerosol systems.

The polymer composition comprises (1) a copolymer of (a) about 35 to 74 weight percent of an alkyl acrylate wherein the alkyl group contains from 1 to 5 carbon atoms; (b) about 25 to 65 weight percent of an alkyl methacrylate wherein the alkyl group contains from 1 to 5 carbon atoms; and (c) about 1 to 15 weight percent of one or more acrylate acids or salts thereof having from 3 to 5 carbon atoms, wherein said copolymer has (i) a glass transition temperature onset of from about 10° to 50° C.; (ii) a number average molecular weight of from about 10,000 to 50,000 g/gmole; (iii) a particle size of from about 0.1 to 1 micron; (2) at least about 0.05 weight percent of a surfactant; and (3) water; wherein said composition has a residual level of said alkyl acrylate of less than 100 parts per million on a weight basis (ppmw) and a Freeze-Thaw Stability Factor (described herein) of at least 3.

DETAILED DESCRIPTION OF THE INVENTION

The polymer compositions of the present invention comprise a copolymer of (a) about 35 to 74 weight percent of an alkyl acrylate wherein the alkyl group contains from 1 to 5 carbon atoms; (b) about 25 to 65 weight percent of an alkyl methacrylate wherein the alkyl group contains from 1 to 5 carbon atoms; and (c) about 1 to 15 weight percent of one or more acrylate acids or salts thereof having from 3 to 5 carbon atoms. More than one monomer species from each of the above monomer groups can be employed in the polymer composition of the present invention.

Preferred alkyl acrylate monomers include methyl acrylate, ethyl acrylate, propyl acrylate and butyl acrylate. Ethyl acrylate is especially preferred. The concentration of alkyl acrylate monomer is preferably from about 40 to 70 weight percent and, more preferably, from about 50 to 60 weight percent of the polymer composition.

Preferred alkyl methacrylate monomers include methyl methacrylate, ethyl methacrylate, propyl methacrylate and butyl methacrylate. Methyl methacrylate is especially preferred. The concentration of alkyl methacrylate monomer is preferably from about 30 to 50 weight percent and, more preferably, from about 30 to 40 weight percent of the polymer composition.

Preferred acrylate acids include acrylic acid, methacrylic acid, crotonic acid, itaconic acid and mixtures thereof. Acrylic acid and methacrylic acid are especially preferred. The concentration of acrylate acids is preferably from about 5 to 15 weight percent and, more preferably, from about 8 to 12 percent of the polymer composition. In one especially preferred aspect of the invention, both acrylic acid and methacrylic acid are employed, each in a concentration range of from about 2 to 10 weight percent, with the total not exceeding about 15 weight percent.

It is also preferred in accordance with the present invention that the copolymer contain only minor amounts, i.e., less than about 10, preferably less than about 5, more preferably less than about 2 and most preferably less than about 1 weight percent, of non-acrylic monomers, e.g., vinyl monomers, as well as only minor amounts of positively charged monomers, e.g., acrylamides. Polymers made from vinyl monomers, e.g., vinyl acetate, can be undesirable because they often contain high levels, e.g., greater than about 100 ppmw, of residual monomers. In addition, cationic or amphoteric polymers can often have poor rinsability. Also it is preferred that the level of hydroxyalkyl acrylate and methacrylate monomers is less than about 5 weight percent, more preferably less than about 1 weight percent of the copolymer.

The polymer compositions of the present invention are typically in colloidal form, i.e., aqueous dispersions, and can be prepared by emulsion polymerization in the presence of a chain transfer agent and an initiator. Specific details concerning procedures and conditions for emulsion polymerization are known to those skilled in the art. Typically, however, the polymerization is carried out in an aqueous medium at a temperature of from about 35° to 90° C. The pressure is not critical and is dependent upon the nature of the monomers employed. Preferably, the copolymer is substantially non-cross-linked, i.e., less than about 1 percent crosslinked.

A chain transfer agent is preferably present during the polymerization reaction at a concentration of from about 0.01 to 5 weight percent, preferably from about 0.1 to 1 weight percent based on the total monomer content. Both water-insoluble and water-soluble chain transfer agents can be employed. Illustrative of substantially water-soluble chain transfer agents are alkyl and aryl mercaptans such as butyl mercaptan, mercaptoacetic acid, mercaptoethanol, 3-mercaptol-1,2-propanediol and 2-methyl-2-propanethiol. Illustrative of the substantially water-insoluble chain transfer agents include, for example, t-dodecyl mercaptan, phenyl mercaptan, pentaerythritol tetramercaptopropionate, octyldecyl mercaptan, tetradecyl mercaptan and 2-ethylhexyl-3-mercaptopropionate.

In carrying out the emulsion polymerization an initiator (also referred to in the art as a catalyst) is preferably used at a concentration sufficient to catalyze the polymerization reaction. This will typically vary from about 0.01 to 3 weight percent based on the weight of monomers charged. However, the concentration of initiator is preferably from about 0.05 to 2 weight percent and, most preferably, from about 0.1 to 1 weight percent of the monomers charged. The particular concentration used in any instance will depend upon the specific monomers mixture undergoing reaction and the specific initiator employed, which details are known to those skilled in the art. Illustrative of suitable initiators include hydrogen peroxide, peracetic acid, t-butyl hydroperoxide, di-t-butyl hydroperoxide, dibenzoyl peroxide, benzoyl hydroperoxide, 2,4-dicholorbenzoyl peroxide, 2,5-dimethyl-2,5-bis(hydroperoxy) hexane, perbenzoic acid, t-butyl peroxypivalate, t-butyl peracetate, dilauroyl peroxide, dicapryloyl peroxide, distearoyl peroxide, dibenzoyl peroxide, diisopropyl peroxydicarbonate, didecyl peroxydicarbonate, dicicosyl peroxydicarbonate, di-t-butyl perbenzoate, 2,2'-azobis-2,4-dimethylvaleronitrile, ammonium persulfate, potassium persulfate, sodium persulfate, sodium perphosphate, azobisisobutyronitrile, as well as any of the other known initiators. Also useful are the redox catalyst systems such as sodium persulfate-sodium formaldehyde sulfoxylate, cumene hydroperoxide-sodium metabisulfite, hydrogen peroxide-ascorbic acid, and other known redox systems. Moreover, as known by those skilled in the art, traces of metal ions can be added as activators to improve the rate of polymerization, if desired.

The particular surfactant useful for conducting the polymerization reaction is not critical to the present invention. Typical surfactants include anionic surfactants such as sodium lauryl sulfate, sodium tridecylether sulfate, diester sulfosuccinates and sodium salts of alkyl aryl polyether sulfonates; and non-ionic surfactants such as alkyl aryl polyether alcohols and ethylene oxide condensates of propylene oxide, propylene glycol adducts.

However, in accordance with the present invention, it has been found that the presence of certain types of surfactants in the final polymer composition can enhance the freeze-thaw stability of the polymer composition. Preferably, the surfactant is effective to inhibit flocculation and viscosity increases due to subjection to freeze-thaw cycles. More preferably, the surfactant is non-ionic, and most preferably, the surfactant is a non-ionic, alkoxylated phenol. It is also especially preferred that the alkoxylated phenol has an alkyl group having from 6 to 12 carbon atoms. One such especially preferred surfactant is an ethoxylated alkyl phenol having an alkyl group with 8 carbon atoms available from Union Carbide Corporation, Danbury, Conn. and sold under the tradename Triton ® X-100. The surfactant, or mixtures of surfactants, added for enhancing freeze-thaw stability can either be introduced with the monomers prior to the polymerization reaction or, alternatively, added to the polymer composition upon completion of the polymerization. Moreover, the surfactants used for freeze-thaw stability can be the same or different from the surfactants used for the polymerization. Preferably the total concentration of surfactants in the polymer composition is from about 0.05 to 0.5 weight percent, more preferably, from about 0.1 to 0.3 weight percent.

As used herein, acceptable freeze-thaw stability means a polymer which has a Freeze-Thaw Stability Factor of at least 3. The Freeze-Thaw Stability Factor is determined as follows. A freeze-thaw test is performed by placing a sample of the polymer composition, e.g., 100 grams, in an environment maintained at a temperature of −5° C. for 16 hours, e.g., a freezer, removing the sample from the cold environment and thawing the sample at a temperature of 20°–25° C. for 8 hours. The freeze-thaw test is repeated three times. After each test, i.e., cycle, an inspection of the polymer composition is made to determine if there has been any flocculation or if there has been a significant change in the viscosity of the polymer composition. For example, if flocculation was observed after the second cycle, the Freeze-Thaw Stability Factor would be 1. If no flocculation or significant change in viscosity occurred after three cycles, the Freeze-Thaw Stability Factor would be 3. For purposes of the present invention, a significant change in the viscosity means an increase in viscosity sufficient to make the polymer composition substantially unpourable, i.e., a gel.

In accordance with the present invention, in addition to providing a surfactant in the polymer composition, the particle size of the copolymer is controlled in order to enhance freeze-thaw stability. It has been found that at particle size levels of less than about 0.1 micron, the freeze-thaw stability is inferior to that of particles larger than 0.1 micron. Particle sizes greater than about 1 micron may provide acceptable freeze-thaw stability, but often can cause particles of the dispersion to settle and are undesirable. Typically, at least 95 weight percent of the copolymer will have an average particle size from about 0.1 to 1 micron, preferably from about 0.1 to 0.5 micron.

In order to control the level of residual monomers remaining in the polymer composition, it is preferred to add an initiator a second time after the polymerization has substantially completed, e.g., greater than about 90 percent conversion. In this manner, it is possible to maintain the level of alkyl acrylate below about 100 ppmw, preferably below about 50 ppmw, and, most preferably, below about 20 ppmw. In addition, it is preferred that the residual level of the other monomers in the composition is less than about 50 ppmw and preferably less than about 20 ppmw for each.

Often, the concentration of copolymer, i.e., solids content, in the polymer composition can be as high as about 50 weight percent, occasionally as high as about 60 weight percent or higher. Preferably, the concentration of copolymer is from about 10 to 60 weight percent and, more preferably, from about 20 to 30 weight percent of the polymer composition.

The pH of the polymer composition typically ranges from about 2 to 8. When the pH is at the low end of the range, it can be increased by introducing a suitable base such as ammonia, alkali metal hydroxides or organic amines. One preferred pH range for the polymer composition is from about 3 to 6 since a lower pH generally provides greater resistance to bacteria, smaller particle size and lower viscosity than a higher pH. Another preferred pH range for the polymer composition is from about 6 to 8, since it is more compatible with skin and hair than the lower pH range.

The viscosity of the polymer composition will typically be from about 1000 to 5000 centipoise at 25° C. The surface tension of the polymer composition will typically be from about 10 to 50 dynes per centimeter at 75° C. It is believed that the low viscosity and surface tension of the polymer compositions contribute to their desirable properties when used in hairspray compositions.

The polymer compositions of the present invention are particularly useful in hairspray compositions. A variety of characteristics are important in assessing the performance of hairspray compositions. Such factors include, for example, stiffness, feel, shine, combability, flaking, curl retention, tinsability, drying time and tackiness.

In accordance with the present invention, certain ranges of number average molecular weight and glass transition temperature onset have been found to provide a desirable balance of the above properties. Accordingly, the number average molecular weight desirably ranges from about 10,000 to 50,000 g/gmole, preferably from about 20,000 to 40,000 g/gmole and more preferably from about 25,000 to 35,000 g/gmole. The glass transition temperature onset desirably ranges from about 10° to 50° C., preferably from about 20° to 40° C., and more preferably from about 25° to 35° C. Methods and apparatus for determining the number average molecular weight and glass transition temperature onset are known to those skilled in the art. However, preferred methods for determining these properties are by gel permeation chromatography and differential scanning calorimetry, respectively. Hairspray compositions made with copolymers having number average molecular weights of less than about 10,000 can have inadequate curl retention. On the other hand, hairspray compositions made with copolymers having number average molecular weight greater than about 50,000 can have inadequate combability. Similarly, hairspray compositions made with copolymers having a glass transition temperature onset of less than about 10° C. can have inadequate curl retention, whereas hairspray compositions made with copolymers having a glass transition temperature onset of greater than about 50° C. can exhibit poor film formation which can lead to excessive flaking, poor shine, and loss of curl retention, for example.

When the polymer compositions of the present invention are used in hairspray compositions, the concentration of copolymer in the hairspray composition is typically from about 1 to 25 weight percent, preferably from about 2 to 18 weight percent and more preferably from about 3 to 15 weight percent of the hairspray composition. The pH is preferably in the range of about 6 to 8 and the surfactant is preferably present in an amount of from about 0.05 to 0.5, and more preferably from about 0.1 to 0.3 weight percent of the hairspray composition. Preferably, the carrier comprises water and, optionally, at least one VOC. The term VOC, as used herein, means any organic compound which is volatile at atmospheric conditions, i.e., 70° F., 14.7 psia. Examples of VOCs include solvents, alcohols having from 1 to 4 carbon atoms, e.g., ethanol and isopropyl alcohol, propellants having from 2 to 6 carbon atoms such as dimethyl ether and alkanes having 1 to 4 carbon atoms, e.g., propane and butane. Quite surprisingly, it has been found that the polymer compositions of the present invention are compatible, i.e., do not form a new phase, with a wide range of carriers and concentrations. The polymer compositions can be formulated into hairspray compositions which have an all aqueous carrier, i.e., where no VOC's are present, or which contain a VOC concentration up to about 80 weight percent, or more.

Typically, water is present in the hairspray composition at a level of from about 2 to 99 weight percent, depending upon concentration of VOCs. Preferred concentrations for water content include from about 2 to 20, about 20 to 50, about 50 to 80, and about 80 to 99 weight percent of the hairspray composition.

Typically, the hairspray composition will be in colloidal form, i.e., a dispersion with the copolymer in the dispersed phase, when the VOC concentration, e.g., ethanol, is less than about 50 weight percent of the hairspray composition. When the VOC concentration is higher than about 50 weight percent, e.g., 80 weight percent, the copolymer may be in solution with the carrier depending on the particular carrier employed. Generally, hairspray compositions in colloidal form are preferred regardless of the VOC content since the colloidal hairspray compositions often provide better performance characteristics, e.g., stiffness, feel, shine, combability, flaking, and curl retention, rinsability, drying time and tackiness.

When the hairspray compositions of the present invention are intended to be delivered by a pump system, the VOCs, if present in the carrier, preferably comprise ethanol, isopropyl alcohol or mixtures thereof. Preferred concentration ranges for alcohol are about 80 weight percent or less, less than about 55 weight percent, less than about 25 weight percent, and less than about 1 weight percent, i.e., substantially free of alcohol. Quite surprisingly, the polymer composition of the present invention has been found to provide excellent spray patterns, atomization characteristics, essentially no clogging and full compatibility throughout the alcohol concentration ranges described above.

When the polymer compositions of the present invention are intended to be delivered by an aerosol system, the VOCs, if present in the carrier, preferably comprise an ether, or mixtures of ethers, having from 2 to 6 carbon atoms, more preferably dimethyl ether. Quite surprisingly, it has been found that ether concentrations in excess of its solubility in water, i.e., about 35 weight percent for dimethyl ether, can be achieved without forming a new, i.e., separate, phase. Preferably, the ether concentration is at least 20 weight percent, more preferably from about 25 to 55 weight percent, and most preferably from about 35 to 45 weight percent of the hairspray composition. It has been found that within the concentration range of about 35 to 45 weight percent, enhanced spray patterns and drying time can be obtained as compared to ether concentrations of 35 weight percent or less. Other propellants known to those skilled in the art, e.g., nitrogen and carbon dioxide, can be used in the hairspray compositions of the present invention. The balance of the carrier can be, for example, water, a VOC such as ethanol, or mixtures thereof.

In addition to the primary ingredients described herein, those skilled in the art will recognize that other desirable ingredients, such as emollients, lubricants, penetrants, proteins, dyes, tints, colorants, perfumes, as well as other ingredients known to those skilled in the art, can be employed in the hairspray compositions of the present invention. Preferably, the additional ingredients will not significantly adversely affect the performance of the hairspray composition.

In addition to the specific aspects described herein, those skilled in the art will recognize that the polymer compositions of the present invention can be utilized in other personal care formulations such as, for example, hair styling gels, mousses, lotions, creams and shampoos.

The following examples are provided for illustrative purposes and are not intended to limit the scope of the claims that follow. All percentages are in weight percent unless otherwise indicated.

EXAMPLES

Table 1, below, provides a cross reference for abbreviations and trade names used in the examples.

TABLE 1

| NAME | DESCRIPTION |
| --- | --- |
| MMA | methyl methacrylate |
| AA | acrylic acid |
| EA | ethyl acrylate |
| MAA | methacrylic acid |
| Aerosol ® OT-100 | an anionic diester sulfosuccinate surfactant available from American Cyanamid, Wayne, NJ. |
| Triton ® X-100 | a nonionic ethoxylated alkyl phenol surfactant available from Union Carbide Corporation, Danbury, CT. |
| Triton ® X-200 | an anionic alkylaryl polyether sulfonate surfactant available from Union Carbide Corporation, Danbury, CT. |
| Dymel ® A | dimethyl ether propellant, available from DuPont, Wilmington, DE. |
| Fluorad ® FC-430 | a nonionic fluorinated surfactant, available from 3M Company, St. Paul, MN. |
| nBM | n-butyl mercaptan |
| 2EHMP | 2-ethylhexyl-3-mercaptopropionate, available from Phillips 66 Company, Bartlesville, OK. |
| PS | volume average particle size, microns |
| Amphomer ® | a terpolymer of an octylacrylamide, butylaminoethyl methacrylate and an acrylate acid, available from National Starch and Chemical, Bridgewater, NJ. |
| Gantrez ® ES-225 | a copolymer of methyl vinyl ether and the ethyl half ester of maleic anhydride, available from International Specialty Products, Wayne, NJ. |
| SD Alcohol 40 | anhydrous ethanol, available from Pharmco Products Inc., Norwalk, CT. |

EXAMPLE 1

PREPARATION of POLYMER COMPOSITION

A copolymer of MMA, EA and MAA was prepared as follows: Five hundred grams of MMA, EA, and MAA were weighed out in the weight ratio of 40/55/5. Half of one weight percent of nBM, based on the total monomer weight, and 0.5 weight percent Aerosol ® OT were added to the monomer mix. Then an initial charge of deionized water (1156 grams) and Aerosol ® OT (1.25 grams) were added to a 3 liter glass-jacketed reaction vessel equipped with a stirrer, condenser, and temperature control. The stirrer was set at 200 revolutions per minute (rpm) for the entire polymerization reaction, the vessel was purged with nitrogen, and the surfactant solution was heated to 80° C. A catalyst solution of 2.5 grams ammonium persulfate and 200 grams deionized water was quickly added to the heated reactor contents. About 5 minutes after adding the catalyst solution, the monomer mix was gradually added over a period of 150 minutes. At the end of the monomer feed, the aqueous dispersion product was maintained at 80° C. for 30 additional minutes. Post initiator solutions, 0.15 grams potassium persulfate in 25 grams water followed by 0.15 grams sodium metabisulfite in 25 grams water, were added and the dispersion was held at 80° C. for another 30 minutes and finally cooled to room temperature.

The resulting dispersion was filtered through a 200 mesh screen and left no scrap. It had a total solids of 26.3 weight percent, a volume average particle size of 0.2 microns, and a pH of 2.5. Its number average molecular weight (Mn) was 21,000 and its glass transition onset (Tg), after equilibrating the polymer at 0% relative humidity for three days, was 30° C.

EXAMPLES 2 TO 18

PREPARATION OF POLYMER COMPOSITIONS

The procedure set forth in Example 1 was used to prepare the polymer compositions set forth in Table 2, below. In Examples 9 to 16 2EHMP was substituted for the chain transfer agent nBM.

TABLE 2

| EXAMPLE | $T_g$ | $M_n$ (× 1000) | PS μ | MMA % | EA % | MAA % | nBM % | ZEHMP % | SOLIDS % |
|---|---|---|---|---|---|---|---|---|---|
| 1 | 30 | 21 | 0.20 | 40 | 55 | 5 | 0.50 | — | 26.3 |
| 2 | 63 | 21 | 0.31 | 65 | 30 | 5 | 0.50 | — | |
| 3 | 28 | 35 | — | 40 | 55 | 5 | 0.25 | — | |
| 4 | 66 | 35 | — | 65 | 30 | 5 | 0.25 | — | |
| 5 | 9 | 10 | — | 35 | 60 | 5 | 1.0 | — | |
| 6 | 18 | 12 | — | 40 | 55 | 5 | 1.0 | — | |
| 7 | 18 | 21 | — | 35 | 60 | 5 | 0.5 | — | |
| 8 | 26 | 22 | — | 40 | 55 | 5 | 0.5 | — | |
| 9 | 28 | 21 | 0.17 | 40 | 55 | 5 | — | 0.8 | 52.0 |
| 10 | 28 | 25 | 0.18 | 37.5 | 55 | 7.5 | — | 0.8 | |
| 11 | 31 | 28 | 0.19 | 34 | 56 | 10 | — | 0.8 | |
| 12 | 33 | 27.3 | 0.13 | 40 | 10 | 0 | — | 0.8 | |
| 13 | 37 | 28.5 | 0.14 | 40 | 12 | 0 | — | 0.8 | |
| 14 | 31 | 27.1 | 0.14 | 37 | 0 | 10 | — | 0.8 | |
| 15 | 33 | 26.1 | 0.14 | 37 | 0 | 12 | — | 0.8 | |
| 16 | 28 | 22.5 | 0.23 | 12 | 83 | 5 | — | 0.72 | |
| *17 | | | 0.08 | 40 | 55 | 5 | — | 0.8 | |
| *18 | | | 0.03 | 37.5 | 55 | 7.5 | — | 0.8 | |

* 2.0 weight percent sodium lauryl sulfate was substituted for 0.3 weight percent Aerosol OT.

EXAMPLES 19 TO 35

PREPARATION OF HAIRSPRAY COMPOSITIONS AND SUBJECTIVE EVALUATIONS

Each of the polymer compositions in Examples 1–18 was formulated into hairspray compositions, first by dilution to 4.0 weight percent total solids using deionized water. The pH was adjusted to 7.5 by adding 0.1 N NaOH dropwise. To prepare hair tresses for testing, forty 23 cm virgin brown hair tresses, each weighing 2 grams, were washed in a 10 weight percent sodium lauryl sulfate solution. Ten washed and color-coded tresses were then dipped into each of the hairspray compositions and the excess solution removed. The hair was rolled on ¾" clean plastic rollers and allowed to dry for 24 hours before testing.

Testing consisted of a subjective evaluation by panelists. For the tests, five curlers from each polymer composition were evaluated for combability, shine, flaking, natural feel, and curl retention. Five panelists rated the tresses on a scale of 1 to 5, 1 being poor and 5 excellent.

Table 3, below, provides an average of the panelists' ratings.

TABLE 3

| EXAMPLE | Polymer (Example) | Combability | Shine | Flaking | Feel | Curl Retention |
|---|---|---|---|---|---|---|
| 19 | 1 | 2.8 | 2.7 | 2.2 | 2.2 | 4.0 |
| 20 | 2 | 3.2 | 2.3 | 1.8 | 3.9 | 2.8 |
| 21 | 3 | 3.0 | 2.6 | 2.8 | 2.2 | 3.8 |
| 22 | 4 | 2.4 | 1.6 | 1.8 | 1.8 | 3.2 |
| 23 | 5 | 2.8 | 3.2 | 4.8 | 3.6 | 3.6 |
| 24 | 6 | 3.6 | 3.8 | 4.8 | 3.8 | 3.6 |
| 25 | 7 | 3.4 | 3.6 | 4.4 | 3.8 | 3.6 |
| 26 | 8 | 2.6 | 3.0 | 4.8 | 3.0 | 4.0 |
| 27 | 9 | 4.0 | 3.8 | 4.8 | 4.0 | 4.0 |
| 28 | 10 | 3.4 | 4.4 | 4.8 | 4.1 | 4.4 |
| 29 | 11 | 3.8 | 4.0 | 4.8 | 3.6 | 4.6 |
| 30 | 12 | 3.3 | 3.8 | 3.0 | 4.3 | 3.3 |
| 31 | 13 | 3.0 | 3.8 | 3.2 | 4.0 | 2.8 |
| 32 | 14 | 3.5 | 3.8 | 3.3 | 3.3 | 3.5 |
| 33 | 15 | 2.3 | 4.0 | 2.5 | 2.5 | 3.8 |
| 34 | 16 | — | — | — | — | — |
| 35 | 17 | 2.6 | 2.8 | 4.0 | 3.8 | 3.2 |

The data show that the polymer compositions from Examples 1 and 8 to 11 provided excellent performance for curl retention, i.e., at least 4.0, which was the one of the most important characteristics judged by the panelists.

Within the group of the polymer compositions from Examples 1 and 8 to 11, the compositions from Examples 10 and 11 also provided excellent shine and flaking resistance, the composition from Example 9 also provided excellent flaking resistance and natural feel and the composition from Example 8 also provided excellent flaking resistance.

EXAMPLE 36

FREEZE-THAW STABILITY

The polymer compositions from Examples 9, 10 and 11 were tested to determine the Freeze-Thaw Stability Factor (described above). At a pH of 8.0, the polymer compositions from Example 9, 10 and 11 had a Freeze-Thaw Stability Factor of 0, 3 and 3, respectively. Between a pH of 5.0 to 7.5, all of the samples had a Freeze-Thaw Stability Factor of 0. By increasing the pH to 8.5, the composition from Example 9 provided a Freeze-Thaw Stability Factor of 3. However, a pH of greater than 8.0 is often undesirable in hairspray compositions.

In order to test the effect of acid content, the acid monomer content of the composition from Example 11 was increased to 10 weight percent. The modified copolymer from Example 11 provided a Freeze-Thaw Stability Factor of 3 at a pH of 5.5.

EXAMPLE 37

FREEZE-THAW STABILITY

Approximately 500 grams of a polymer composition having similar characteristics to that described by Example 9 was diluted with water to contain approximately 25 percent solids. The viscosity of the diluted polymer composition, as measured with a Brookfield RV Viscometer having a #2 spindle at 6 rpm, was approximately 4000 centipoise. The pH of the polymer composition was adjusted by adding sodium hydroxide drop-wise until a pH of about 7.2 was obtained. A 100 gram sample of the modified polymer composition was subjected to the freeze-thaw test. After one cycle, the polymer flocculated and the viscosity had increased to the point where the composition was almost unpourable. In order to determine the effect of various surfactants in the polymer composition, 4 additional samples of the modified polymer composition were further modified by introducing approximately 0.2 grams of surfactant (approximately 0.2 weight percent) to each of the samples. The samples were then subjected to the freeze-thaw test. Table 4 below sets forth the results from the freeze-thaw test.

TABLE 4

| Surfactant | Freeze-Thaw Stability Factor |
| --- | --- |
| Triton ® X-100 | 3 |
| Triton ® X-200 | 0 |
| Fluorad ® FC-430 | 0 |
| Aerosol ® OT-100 | 0 |

The data show that the surfactant providing the best degree of freeze-thaw stability was Triton X-100. The Fluorad ® FC-430 caused less viscosity increase than the Triton ® X-200 and Aerosol ® OT-100. Accordingly, it is believed that surfactants which are non-ionic can provide enhanced freeze-thaw stability over surfactants which are ionic.

EXAMPLE 39

PREPARATION of HAIRSPRAY COMPOSITIONS CONTAINING ETHANOL

Approximately 335 grams of deionized water were added to a 1 liter capacity glass beaker. A magnetic stirrer apparatus was used to agitate the water in the beaker at a high speed. Approximately 1.0 gram of Triton ® X-100 was added to the deionized water and the agitation was continued until completely dissolved. Approximately 100 grams of SD Alcohol were introduced and mixed for 5 minutes. Then approximately 60 grams of the polymer composition described in Example 9 were introduced and agitated for 5 minutes. Approximately 1.2 grams of a 5 percent solution of sodium hydroxide were introduced and mixed for 10 minutes.

EXAMPLE 39 TO 42

PERFORMANCE OF HAIRSPRAY COMPOSITIONS CONTAINING ETHANOL

The polymer composition of Example 9 was formulated in accordance with the procedure of Example 38 to provide hair spray compositions with ethanol concentrations of 0, 20 and 50 weight percent (Examples 39 to 41) and a copolymer concentration of 4 weight percent. The subjective tests described with reference to Examples 19 to 35 were used to evaluate the hair spray compositions. Final Net hairspray (regular hold), a commercially available hair spray containing Gantrez ® ES-225, was used as a comparative example (Example 42). The evaluation data is set forth in Table 5 below.

TABLE 5

| EXAMPLE | Polymer (Example) | Combability | Shine | Flaking | Feel | Curl Retention |
| --- | --- | --- | --- | --- | --- | --- |
| 39 | 9 | 3.8 | 4.2 | 4.8 | 3.2 | 3.6 |
| 40 | 9 | 3.6 | 4.2 | 4.8 | 4.6 | 4.0 |
| 41 | 9 | 3.9 | 4.0 | 4.8 | 3.8 | 3.8 |
| 42 | — | 3.9 | 4.0 | 4.8 | 3.5 | 3.6 |

The data demonstrate that the polymer compositions of the present invention can be formulated with a wide range of alcohol content and provide performance comparable to or better than a commercial product.

EXAMPLE 44

COMPATIBILITY WITH ALCOHOL

Polymer compositions similar to that described in Example 9 were formulated in accordance with the procedure of Example 38 to provide hairspray compositions with ethanol concentrations of 0, 20, 50 and 80 weight percent, with a copolymer concentration of about 4 weight percent. All of the samples were fully compatible with the carrier, i.e., did not form a separate phase from the emulsion phase. Each of the above hairsprays was evaluated for spray pattern, drying time, tackiness and flaking and all samples were found to have acceptable characteristics in each of these categories. In addition, when comparing the hairspray containing 80 percent ethanol with Rave 3 hairspray, a commercially available hairspray composition containing Amphomer ®, it was found that the hairspray of the present invention provided a faster drying time and had less tackiness.

EXAMPLE 45

PREPARATION OF AEROSOL HAIRSPRAY COMPOSITIONS

An aerosol hairspray composition was prepared by first preparing a hairspray composition in accordance with the procedure described in Example 38. Approximately 30 grams of the hairspray composition described in Example 38 was added to a glass compatibility bottle having a 120 milliliter capacity and 20 millimeter neck size. A standard 20 millimeter aerosol valve was crimped with a dip tube onto the bottle. Using conventional aerosol filling techniques, approximately 20 grams of Dymel ® A were introduced into the bottle.

EXAMPLE 46

PERFORMANCE OF AEROSOL HAIRSPRAY COMPOSITIONS

Aerosol hairspray compositions were prepared following the procedure described in Example 45 which contained 30, 40 and 45 weight percent Dymel ® A. Each of the aerosol hairspray compositions was completely compatible with the propellant. Each of the samples was evaluated for spray pattern, drying time and tackiness. Quite surprisingly, it was found that the samples containing 40 and 45 weight percent Dymel ® A did not form a separate phase and provided an enhanced spray pattern, a shorter drying time and less tackiness than the aerosol hairspray composition containing 30 percent Dymel ® A.

EXAMPLE 47

PREPARATION OF IMINATED POLYMER COMPOSITION

A copolymer of MMA, EA, AA and MAA was prepared as follows: Five hundred grams of MMA, EA, AA and MAA were weighed out in the weight ratio of 31/59/5/5. Half of one weight percent of 2EHMP, based on the total monomer weight, and 0.5 weight percent Aerosol ® OT were added to the monomer mix. Then an initial charge of deionized water (480 grams) and Aerosol ® OT (1.25 grams) were added to a 3 liter glass-jacketed reaction vessel equipped with a stirrer, condenser, and temperature control. The stirrer was set at 200 rpm for the entire polymerization reaction, the vessel was purged with nitrogen, and the surfactant solution was heated to 80° C. A catalyst solution of 2.5 grams ammonium persulfate and 25 grams deionized water was quickly added to the heated reactor contents. About 5 minutes after adding the catalyst solution, the monomer mix was gradually added over a period of 150 minutes. At the end of the monomer feed, the aqueous dispersion product was maintained at 80° C. for 30 additional minutes. A post initiator solution of 0.10 gram ammonium persulfate in 1.0 gram water was added and the dispersion was held at 80° C. for another 30 minutes and finally cooled to room temperature.

The resulting dispersion was filtered through a 200 mesh screen and left no scrap. It had a total solids of 51.2 weight percent, a volume average particle size of 0.2 microns, and a pH of 2.6. Its Mn was 27,000 and its Tg, after equilibrating the polymer at 0% relative humidity for three days, was 25° C.

The first step in iminating this sample was to dilute it to 25 weight percent total solids. Then 820 grams of the polymer composition were charged to a 2 liter reaction vessel like the one described above. It was heated to 50° C. with an agitation of 350 rpm. At this point, 24 grams of a 25 weight percent aqueous propylene imine solution were added and the latex was allowed to stir for 1 hour at 50° C. After cooling, the pH was 7.0 and the appearance was that of a white, low-viscosity latex.

EXAMPLE 48

PERFORMANCE OF IMINATED POLYMER COMPOSITION

For this experiment, the performance of the iminated polymer composition of Example 47 was compared with the same polymer composition except without imination. The two polymer compositions were formulated into hairspray compositions in accordance with the procedure set forth in Examples 19 to 35 to provide hairspray compositions containing 6 weight percent copolymer, 0.10 weight percent Triton ® X-100, with the balance being deionized water. The pH was adjusted to 7.5–8.0 with sodium hydroxide.

The two hairspray compositions were then evaluated for freeze-thaw stability, rinsability, drying time and whitening effect. In order to determine rinsability, about 1 gram of the hairspray composition was sprayed on a watch glass and allowed to dry for 12 hours, and then rinsed with water at 28° C. In addition, about 2.0 grams of the hairspray composition were applied to a 5.0 gram hair tress, allowed to dry for 3 hours, and washed with Rave 3 shampoo (commercially available). In order to determine drying time, about 0.25 gram of the hairspray composition was applied to a watch glass, and the time to dry at 70 percent relative humidity was recorded. The whitening effect was observed during drying. In general, whitening during drying is highly undesirable. The results of the rinsability drying time and whitening tests, along with the Freeze-Thaw Stability Factor, is set forth in Table 6 below.

TABLE 6

| Hairspray Composition | Freeze-Thaw Stability Factor | Rinsability Glass | Rinsability Hair | Drying Time (minutes) | Whitening |
|---|---|---|---|---|---|
| HC | 3 | Good | Good | 40 | Good |
| HCi (iminated) | 3 | Poor | Marginal | 50 | Poor |

The hairspray compositions were also evaluated for combability, shine, flaking, feel and curl retention by the panelists' tests as described in Examples 19 to 35.

The results of the panelists' evaluations are set forth in Table 7 below.

TABLE 7

| Hairspray Composition | Combability | Shine | Flaking | Feel | Curl Retention |
|---|---|---|---|---|---|
| HS | 2.4 | 3.9 | 3.9 | 3.9 | 2.9 |
| HSi | 3.2 | 4.2 | 4.1 | 4.2 | 3.1 |

The above data show that although the iminated polymer composition provided a hairspray composition having subjective properties slightly better than the uniminated hairspray composition, the drying time was 25 percent longer for the iminated hairspray composition and the tinsability and whitening were inferior. Thus, the deficiencies in drying time, rinsability and whitening outweigh the slight improvement observed in the subjective evaluation. Stated another way, it is seen from the data that partial imination does not significantly improve the performance of the hairspray, i.e., subjective properties: in fact it introduces serious deficiencies in rinsability, drying time and whitening effect.

We claim:

1. An aqueous, anionic polymer composition comprising:

(1) from about 10 to 60 weight percent of a copolymer of: (a) about 35 to 74 weight percent of an alkyl acrylate selected from the group consisting of methyl acrylate, ethyl acrylate, propyl acrylate, butyl acrylate and mixtures thereof (b) about 25 to 65 weight percent of an alkyl methacrylate selected from the group consisting of methyl methacrylate, ethyl methacrylate, propyl methacrylate, butyl methacrylate and mixtures thereof and (c) about 1 to 15 weight percent of one or more acrylate acids or salts thereof selected from the group consisting of acrylic acid, methacrylic acid, crotonic acid, itaconic acid and mixtures thereof, wherein said copolymer has (i) a glass transition temperature onset of from about 10° to 50° C.; (ii) a number average molecular weight of from about 10,000 to 50,000 g/g mole; (iii) a particle size of from greater the 0.1 to about 1 micron;

(2) from about 0.05 to 0.5 weight percent of a nonionic, alkoxylated phenol surfactant containing an alkyl group having from 6 to 12 carbon atoms; and (3) water;

wherein said composition has a Freeze-Thaw Stability Factor of at least 3 and a residual level of said alkyl acrylate of less than 100 ppmw.

2. The composition of claim 1 wherein the particle size of the copolymer is from greater than 0.1 to about 0.5 microns.

3. The composition of claim 1 wherein the glass transition temperature onset is from about 25° to 35° C.

4. The composition of claim 1 wherein the number average molecular weight is from about 25,000 to 35,000 g/gmole.

5. The composition of claim 1 having a pH of from about 2 to 8.

6. The composition of claim 1 comprising from about 50 to 60 weight percent ethyl acrylate, from about 30 to 40 weight percent methyl methacrylate, from about 2 to 10 weight percent acrylic acid and from about 2 to 10 weight percent methacrylic acid, provided that the total concentration of acrylic acid and methacrylic acid does not exceed about 15 weight percent.

7. The composition of claim 1 wherein the concentration of the surfactant is from about 0.1 to 0.3 weight percent.

8. The composition of claim 1 wherein concentration of acrylate acids is from about 5 to 15 weight percent.

9. The composition of claim 8 wherein concentration of acrylate acids is from about 8 to 12 weight percent.

10. The composition of claim 1 wherein the copolymer comprises less than about 1 weight percent of non-acrylic monomers.

11. The composition of claim 10 wherein the copolymer comprises less than about 1 weight percent of vinyl monomers.

12. The composition of claim 1 wherein the copolymer comprises less than about 1 weight percent of positively charged monomers.

13. The composition of claim 12 wherein the copolymer comprises less than about 1 weight percent of acrylamide monomers.

14. The composition of claim 1 wherein the copolymer comprises less than about 1 weight percent of hydroxyalkyl acrylate and methacrylate monomers.

15. A hairspray composition comprising:
(1) from about 1 to 25 weight percent of a copolymer of; (a) about 35 to 74 weight percent of an alkyl acrylate selected from the group consisting of methyl acrylate, ethyl acrylate, propyl acrylate, butyl acrylate and mixtures thereof (b) about 25 to 65 weight percent of an alkyl methacrylate selected from the group consisting of methyl methacrylate, ethyl methacrylate, propyl methacrylate, butyl methacrylate and mixtures thereof and (c) about 1 to 15 weight percent of one or more acrylate acids or salts thereof selected from the group consisting of acrylic acid, methacrylic acid, crotonic acid, itaconic acid and mixtures thereof, wherein said copolymer has (i) a glass transition temperature onset of from about 10° to 50° C.; (ii) a number average molecular weight of from about 10,000 to 50,000 g/g mole; (iii) a particle size of from greater than 0.1 to about 1 micron;

(2) from about 0.05 to 0.5 weight percent of a nonionic, alkoxylated phenol surfactant containing an alkyl group having from 6 to 12 carbon atoms; and (3) a carrier comprising water and up to about 80 weight percent of a volatile organic compound selected from the group consisting of alcohols having from 1 to 4 carbon atoms, alkanes having from 1 to 4 carbon atoms, ethers having from 2 to 6 carbon atoms, and mixtures thereof;

wherein said composition has a Freeze-Thaw Stability Factor of at least 3 and a residual level of said alkyl acrylate of less than 100 ppmw.

16. The composition of claim 15 wherein the surfactant is present in an amount of from about 0.1 to 0.3 weight percent.

17. The composition of claim 15 wherein the pH of the composition is from about 6 to 8.

18. The composition of claim 15 which contains up to about 55 weight percent volatile organic compounds.

19. The composition of claim 15 which comprises less than about 1 weight percent of alcohol.

20. The composition of claim 15 which comprises from about 3 to 15 weight percent of the copolymer.

21. The composition of claim 15 wherein the volatile organic compounds are selected from the group consisting of ethanol, isopropyl alcohol, dimethyl ether and mixtures thereof.

22. The composition of claim 21 which comprises from about 25 to 55 weight percent dimethyl ether.

23. The composition of claim 22 which comprises from about 35 to 45 weight percent dimethyl ether.

24. An aqueous, anionic polymer composition comprising:
(1) from about 10 to 60 weight percent of a copolymer consisting essentially of from about 50 to 60 weight percent ethyl acrylate, from about 30 to 40 weight percent methyl methacrylate from about 2 to 10 weight percent acrylic acid and from about 2 to 10 weight percent methacrylic acid, provided that the total concentration of acrylic acid and methacrylic acid does not exceed about 15 weight percent; wherein said copolymer has (i) a glass transition temperature onset of from about 25° to 35° C.; (ii) a number average molecular weight of from about 25,000 to 35,000 g/gmole; (iii) a particle size of from greater than 0.1 to about 1 micron;

(2) from about 0.05 to 0.5 weight percent of a nonionic, alkoxylated phenol surfactant containing an alkyl group having from 6 to 12 carbon atoms; and (3) water;

wherein said composition has a Freeze-Thaw Stability Factor of at least 3 and a residual level of said alkyl acrylate of less than 100 ppmw.

25. An aqueous, anionic polymer composition comprising:
(1) from about 10 to 60 weight percent of a copolymer of (a) about 35 to 74 weight percent of an alkyl acrylate wherein the alkyl group contains from 1 to 5 carbon atoms; (b) about 25 to 65 weight percent of an alkyl methacrylate wherein the alkyl group contains from 1 to 5 carbon atoms; and (c) about 1 to 15 weight percent of one or more acrylate acids or salts thereof having from 3 to 5 carbon atoms, wherein said copolymer has (i) a glass transition temperature onset of from about 10° to 50° C.; (ii) a number average molecular weight of from about 10,000 to 50,000 g/gmole; (iii) a particle size of from greater than 0.1 to about 1 micron;
(2) from about 0.05 to 0.5 weight percent of a nonionic, alkoxylated phenol surfactant; and
(3) water;
wherein said composition has a Freeze-Thaw Stability Factor of at least 3 and the copolymer comprises less than about 1 weight percent of non-acrylic monomers, less than about 1 weight percent of positively charged monomers and less than about 1 weight percent of hydroxyalkyl acrylate and methacrylate monomers and a residual level of said alkyl acrylate of less than 100 ppmw.

26. The composition of claim 25 wherein the surfactant is ethoxylated.

27. The composition of claim 26 wherein the surfactant contains an alkyl group having from 6 to 12 carbon atoms.

28. The composition of claim 27 wherein the surfactant contains an alkyl group having 8 carbon atoms.

29. The composition of claim 25 wherein said copolymer has a particle size of from about 0.13 to 0.31 micron.

* * * * *